United States Patent [19]
Baker

[11] Patent Number: 5,261,813
[45] Date of Patent: Nov. 16, 1993

[54] ORTHODONTIC'S HAND INSTRUMENT AND METHOD

[76] Inventor: Melvin B. Baker, 7405 N.W. 23rd, Bethany, Okla. 73008

[21] Appl. No.: 911,431
[22] Filed: Jul. 10, 1992
[51] Int. Cl.$^5$ .............................................. A61C 3/00
[52] U.S. Cl. .......................................... 433/3; 433/4; 433/157; 433/159; 433/162
[58] Field of Search ................. 433/3, 4, 153, 157, 433/159, 162

[56] References Cited

U.S. PATENT DOCUMENTS

| | | | |
|---|---|---|---|
| 450,266 | 4/1891 | Truax | 606/210 |
| 536,166 | 3/1895 | Angle | 433/4 |
| 1,034,591 | 8/1912 | Douds | 433/4 |
| 1,064,404 | 6/1913 | Walker | 433/4 |
| 1,545,693 | 7/1925 | Phoel | 294/99.2 |
| 1,670,361 | 5/1928 | Johnson | 433/4 |
| 3,291,476 | 12/1966 | Calkin | 269/254 |
| 4,260,374 | 4/1981 | Kurz | 433/3 |
| 4,285,344 | 8/1981 | Marshall | 433/159 |
| 4,487,580 | 12/1984 | Rideway | 433/3 |
| 5,007,827 | 4/1991 | DiFranco | 433/4 |

Primary Examiner—John J. Wilson
Attorney, Agent, or Firm—Dunlap, Codding & Lee

[57] ABSTRACT

An orthodontic's hand instrument for installing a lingual bar on the lower arch of a patient's teeth. The hand instrument includes a handle having a first end and a second end with a clamp connected to the second end of the handle. A portion of the clamp extends a distance downwardly from the handle and another portion of the clamp extends a distance back toward the first end of the handle terminating with a clamp end. The clamp is movable to an opened position whereby a portion of the clamp near the clamp end is insertable over a portion of the lingual bar and the clamp is movable to a closed position whereby a portion of the clamp near the clamp end is clampingly closed over a portion of the lingual bar for clampingly holding the lingual bar. The clamp holding the lingual bar is movable into the patient's mouth and lowerable to position the lingual bar near the lingual side of the patient's lower teeth for connecting opposite ends of the lingual bar to the patient's lower teeth.

25 Claims, 1 Drawing Sheet

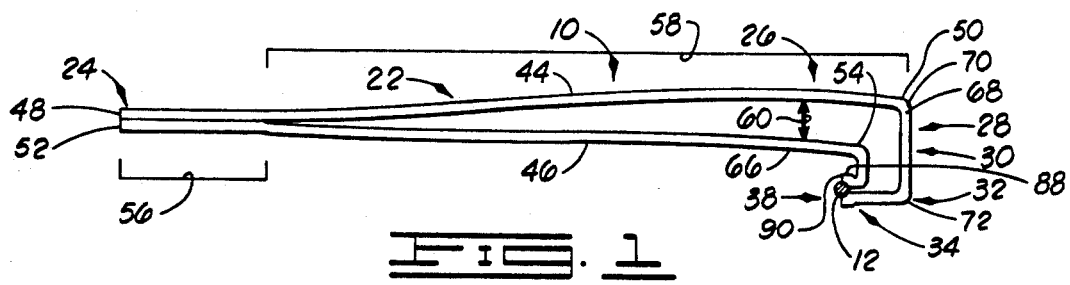
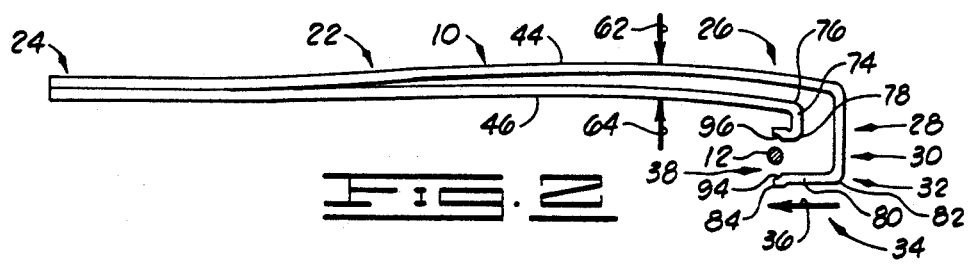
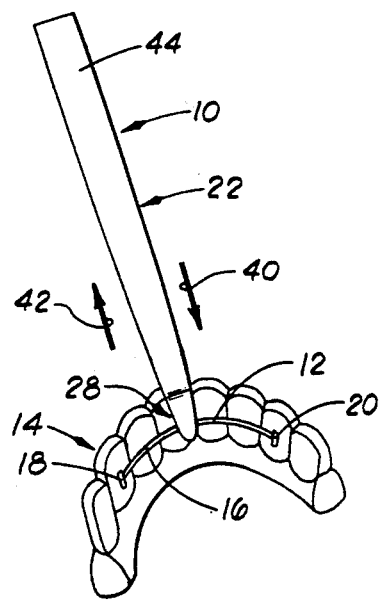
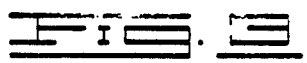
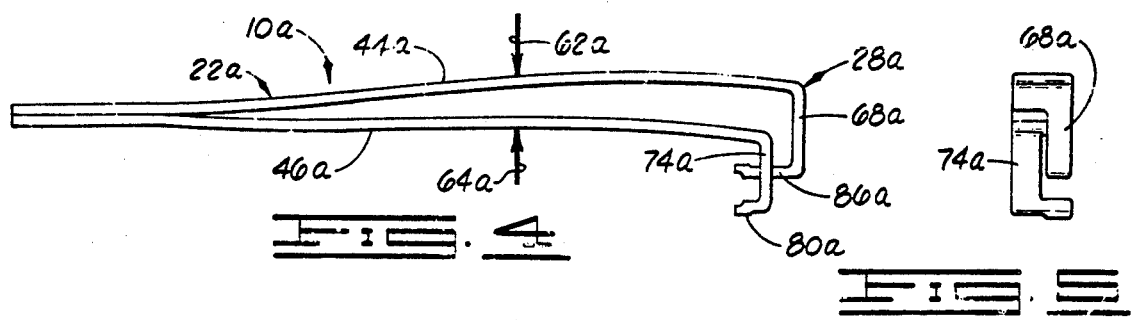

ORTHODONTIC'S HAND INSTRUMENT AND METHOD

FIELD OF THE INVENTION

An orthodontic's hand instrument for installing a lingual bar on a patient's lower teeth and, more particularly, an orthodontic's hand instrument having a handle with a first and a second end and with a clamp connected to the second end of the handle, the clamp being movable to an opened position whereby a portion of the clamp is insertable over a portion of the lingual bar and the clamp being movable to a closed position whereby a portion of the clamp is clampingly closed over a portion of the lingual bar for clampingly holding the lingual bar, the clamp end being insertable into a patient's mouth and lowerable to position the lingual bar near the lingual side of the patient's lower teeth for connecting the lingual bar to the patient's lower teeth.

BRIEF DESCRIPTION OF THE DRAWINGS

FIG. 1 is a side elevational view of an orthodontic's hand instrument constructed in accordance with the present invention showing a clamp portion of the hand instrument clampingly connected to a lingual bar, the lingual bar being shown in cross-section.

FIG. 2 is a side elevational view of the hand instrument of FIG. 1 showing the clamp portion of the hand instrument in the opened position for receiving a portion of the lingual bar, the lingual bar being shown in cross-section.

FIG. 3 is a diagrammatic, perspective view of the hand instrument of FIG. 1 showing the hand instrument clampingly connected to the lingual bar with the clamp portion of the hand instrument being inserted over a portion of a patient's lower teeth and positioning the lingual bar near the lingual side of a portion of the patient's lower teeth.

FIG. 4 is a side elevational view, similar to FIG. 1, but showing a modified orthodontic's hand instrument.

FIG. 5 is a front elevational view of the modified orthodontic's hand instrument of FIG. 4.

DESCRIPTION OF THE PREFERRED EMBODIMENTS

Braces commonly are installed by a dentist on a patient's teeth for the purpose of correcting alignment of the patient's teeth. When the braces are removed by the dentist, it is common to stabilize the lower arch of the patient's lower teeth with a lingual bar to prevent movement of the lower teeth. If the lower teeth are allowed to shift, this will result in a corresponding undesirable shift in the patient's upper teeth. The lingual bar is utilized to prevent the undesirable shifting of the lower or upper teeth after the braces have been removed from the patient's teeth.

In the past, the dentist has gripped the lingual bar with the dentist's fingers. The dentist then has been required to move the lingual bar held by his fingers into the patient's mouth and then attempt to properly position the lingual bar adjacent the lingual side of the patient's lower teeth. This procedure has been relatively difficult and time consuming.

The present invention provides an orthodontic's hand instrument designed to assist the dentist in inserting the lingual bar into the patient's mouth and properly position the lingual bar adjacent the lingual side of a patient's lower teeth in a relatively quick and convenient manner.

Referring to the drawings in general and to FIGS. 1 and 2 in particular, shown therein and designated by the general reference numeral 10 is an orthodontic's hand instrument constructed in accordance with the present invention for installing a lingual bar 12 (FIGS. 1, 2 and 3) on the lingual side of a patient's lower teeth 14 (diagrammatically shown in FIG. 3 and designated therein by the general reference numeral 14).

The lingual bar 12 (FIG. 3) comprises a cylindrically shaped bar section 16 With flanges 18 and 20 formed on the opposite ends of the bar section 16. The bar section 16 is arcuately shaped to generally conform to the lingual side of the lower arch of the patient's lower teeth 14.

As shown more clearly in FIGS. 1 and 2, the hand instrument 10 comprises a handle 22 having a first end 24 and a second end 26. A clamp 28 is connected to the second end 26 of the handle 22.

As shown in FIGS. 1 and 2) the clamp 28 has a first clamp portion 30 which extends a distance downwardly about perpendicularly from the handle 22 terminating with a lower end 32. The clamp 28 includes a second clamp portion 34 which is connected to the lower end 32 of the first clamp portion 30. The second clamp portion 34 extends at an angle of about 90° from the first clamp portion 30 in a direction 36 (FIG. 2) generally toward the first end 24 of the handle 22 terminating with a clamp end 38.

The clamp 28 is movable by the dentist manipulating handle 22 to an opened position (FIG. 2) whereby the clamp end 28 is insertable over a portion of the lingual bar 12. The clamp 28 also is movable by the dentist manipulating the handle 22 to a closed position (FIG. 1) whereby the clamp end 38 of the clamp 28 clampingly engages and clampingly holds a portion of the lingual bar 12.

In operation, the handle 22 is manipulated by the dentist to move the clamp 28 to the opened position. The clamp end 38 then is inserted over a portion of the lingual bar 12. The dentist then manipulates the handle 22 to move the clamp 28 to the closed position whereby the clamp end 38 of the clamp 28 clampingly engages and holds the lingual bar 12.

The dentist manipulates the handle 22 to move the clamp 28 in the insert direction 40 (FIG. 3) over the patient's lower teeth 14 and into the patient's mouth. The dentist then manipulates the handle 22 to lower the clamp end 38 of the clamp 28 downwardly and then back in a direction out of the patient's mouth to position the lingual bar 12 generally adjacent the lingual side of the patient's lower teeth 14.

After the lingual bar 12 has been connected to the patient's lower teeth 14, the dentist then manipulates the handle 22 to move the clamp 28 to the opened position thereby releasing the lingual bar 12 from the clamp end 38 of the clamp 28. The lingual bar 12 is connected to the patient's lower teeth 14. The dentist then removes the clamp end 38 of the clamp 38 from the lingual bar 12 thereby leaving the lingual bar 12 installed on or connected to the lingual side of the patient's lower teeth 14. After the lingual bar 12 has been installed on the patient's lower teeth, the dentist removes the clamp 28 from the patient's mouth by moving the clamp 28 in the upwardly direction to a position wherein the clamp is disposed above the lower teeth 14, and the dentist then moves the handle 22 and clamp 28 connected thereto in a removal direction 42 (FIG. 3), generally opposite the insert direction 40.

As shown in FIG. 3, the flanges 18 and 20 on the lingual bar 12 more particularly are connected to the cuspid incisors of the patient's lower teeth 14. The lingual bar 12 in some instances is connected to the lateral incisors or the first bicuspids of the patient's lower teeth.

Commonly, a light activated adhesive is placed on the lingual side of the patient's lower teeth at positions where the lingual bar 12 is to be connected. The dentist then positions the lingual bar 12 with the flanges 18 and 20 disposed over or on the light activated adhesive. The dentist light activates the adhesive to secure the lingual bar 12 on the lingual side of the patient's lower teeth 14. The dentist then releases the lingual bar from the hand instrument 10 and removes the hand instrument 10 from the patient's mouth. It should be noted that, in some instances, a two component adhesive can be used to attach the lingual bar 12 to the patient's lower teeth 14. In this instance, it is not necessary to use light to activate the adhesive. However, this type of two component adhesive generally limits the time within which the dentist has to secure the lingual bar 12 to the patient's lower teeth 14 which may not be desirable in some applications.

The handle 22 and the clamp 28 are sized and constructed of a material suitable for insertion into a patient's mouth.

The handle 22 more particularly comprises a first handle arm 44 and a second handle arm 46. The first handle arm 44 has a first end 48 (FIG. 1) and a second end 50 (FIG. 1). The second handle arm 46 comprises a first end 52 (FIG. 1) and a second end 54 (FIG. 1).

A first portion 56 (FIG. 1) of the first handle arm 44 near the first end 48 thereby is connected to a portion of the second handle arm 46 near the first end 52 thereof. A second portion 58 of the handle 22 extends a distance from the first portion 56 and terminates with the second end 26 at the handle 22. The first handle arm 44 extends a distance angularly from the first portion 56 of the handle 22 and the second handle arm 46 also extends at a distance angularly from the first portion 56. The first handle arm 44 extends angularly from the second handle arm 46 whereby the first and the second handle arms 44 and 46 are spaced apart a distance 60 (FIG. 1). The first and the second arms 44 and 46 are springly held the distance 60 (FIG. 1) apart in the closed position of the clamp 28.

The first and the second handle arms 44 and 46 are movable in the respective directions 62 and 64 (FIG. 2) by the dentist pressing the first and the second arms 44 and 46 in the respective directions 62 and 64 thereby moving the first handle arm 44 in the direction 62 and moving the second handle arm 64 in the direction 64 generally toward each other thereby decreasing the distance 60 between the first and the second arms 44, thereby moving the clamp 28 to the opened position. When the dentist releases this compressing hold on the first and the second handle arms 44 and 46, the first and the second arms 44 and 46 springly move back in directions opposite the directions 62 and 64 to position the clamp 28 in the closed position whereby the first and the second handle arms 44 and 46 are springly held the distance 60 apart.

The first ends 48 and 52 of the first and the second handle arms 44 and 46 cooperate to form the first end 24 of the handle 22. The second ends 50 and 54 of the first and the second handle arms 44 and 46 cooperate to form the second end 26 of the handle 22.

A lower surface of the second handle arm 46 forms a lower surface 66 (FIG. 1) of the handle 22.

The clamp 28 more particularly comprises a first clamp arm 68 (FIG. 1) having a first end 70 (FIG. 1) and a second end 72 (FIG. 1). The first end 70 of the first clamp arm 68 is connected to the second end 50 of the first handle arm 44 and the first clamp arm 68 extends a distance about perpendicularly downwardly from the first handle arm 44 terminating with the second end 72 of the first clamp arm 68.

The clamp 28 also includes a second clamp arm 74 (FIG. 2) having a first end 76 (FIG. 2) and a second end 78 (FIG. 2). The first end 76 of the second clamp arm 74 is connected to the second end 54 of the second handle arm 46 and the second clamp arm 74 extends a distance about perpendicularly from the second handle arm 46 terminating with the second end 78 of the second clamp arm 74.

The first and the second clamp arms 68 and 74 cooperate to comprise the first clamp portion 30 of the clamp 28.

The clamp 28 also includes a third clamp arm 80 (FIG. 2) having a first end 82 (FIG. 2) and a second end 84 (FIG. 3). The first end 82 of the third clamp arm 80 is connected to the second end 72 of the first clamp arm 68. The third clamp arm 80 extends a distance about perpendicularly from the first clamp arm 68 in the direction 36 generally toward the first end 26 of the handle 22.

The clamp 28 also includes a fourth clamp arm 86 (FIG. 1) having a first end 88 (FIG. 1), a second end 90 (FIG. 1). The first end 88 of the fourth clamp arm 86 is connected to the second end 78 of the second clamp arm 74. The fourth clamp arm 86 extends a distance about perpendicularly from the second clamp arm 74 and the direction 36 generally toward the first end 24 of the handle 22.

The second ends 84 and 90 of the third and the fourth clamp arms 80 and 86 comprise the clamp end 38 of the clamp 28.

A circularly shaped recess 94 (FIG. 2) is formed in the second end 84 of the third clamp arm 80. A circularly shaped recess 96 (FIG. 2) is formed in the second end 90 of the fourth clamp arm 86. The circularly shaped recesses 94 and 96 are shaped to conform to the outer peripheral surface of the lingual bar 12 so that the lingual bar 12 fits within the circularly shaped recesses 94 and 96 when the lingual bar 12 is connected to the clamp end 38 of the clamp 28, as shown in FIG. 1.

The fourth clamp arm 86 is spaced a distance 100 from the lower surface 66 of the handle 22. The distance 100 is sufficient so that the clamp end 38 of the clamp 28 can be lowered to position the lingual bar 12 adjacent the lingual side of the lower teeth 14 without the handle 22 interferringly engaging the lower teeth 14.

In operation, when the dentist compress the first and the second handle arms 44 and 46 in the respective directions 62 and 64, the third clamp arm 80 is moved in the direction 98 and the fourth clamp arm 86 is moved in the general direction 100 thereby moving the third clamp arm 80 generally away from the fourth clamp arm 86 to a position wherein the third clamp arm 80 is spaced a distance from the fourth clamp arm 86 as shown in FIG. 2 in the opened position of the clamp 28. When the dentist releases the compressing forces on the first and the second handle arms 44 and 46, the first and the second handle arms 44 and 46 are moved in a direction generally away from each other opposite the directions 62 and 64 thereby moving the third clamp arm 80 toward the fourth clamp arm 86 in directions opposite the directions 98 and 100 thereby moving the third clamp arm 80 to a position generally adjacent the fourth clamp arm 86 in moving the clamp 28 to the closed position (FIG. 1).

EMBODIMENTS OF FIGS. 4 AND 5

Shown in FIGS. 4 and 5 is a modified hand instrument 10a which is constructed exactly like the hand instrument 10 shown in FIGS. 1, 2 and 3 and described in detailed before, except the third clamp arm 80a is angled and crossed over the fourth clamp arm 86a so that the fourth clamp arm 86a is disposed above the third clamp arm 80a.

The hand instrument 10a will operate exactly like the hand instrument 10 described in detail before, except, when the dentist compresses the first and the second handle arms 44a and 46a in the directions 62a and 64a the third clamp arm 80a will be moved in a direction generally toward the fourth clamp arm 86a and the fourth clamp arm 86a will move in a direction generally toward the third clamp arm 80a thereby moving the third and fourth clamp arms 80a and 86a toward the closed position. By the same token, when the dentist releases the pressure on the first and the second handle arms 44a and 46a, the first and the second handle arms 44a and 46a are moved in opposite directions thereby moving the first and the second handle arms 44a and 46a generally apart from each other, thereby moving the third and the fourth clamp arms 80a and 86a generally away from each other to the opened position of the clamp 28a.

The hand instrument 10a thus is moved to the closed position by the dentist compressing the handle arms 44a and 46a and the hand instrument 10a is moved to the opened position of the clamp 28a by the dentist releasing the compressing force on the handle arms 44a and 46a. This in essence is the reverse action of the dentist manipulating the handle 22 shown in FIGS. 1, 2 and 3 to move the clamp 28 to the opened and the closed positions. With respect to the hand instrument 10a the dentist controls the clamping force applied to the lingual bar 12 by the clamp 28a by the amount of force applied by the dentist to the first and the second handle arms 44a and 46a. This may be desirable in some applications, rather than relying on the springing action on the first and the second handle arms 44 and 46 of the hand instrument 10 to apply the clamping force to the clamp 28 of the hand instrument 10.

The first and the second handle arms 44 and 46 also could be constructed so that one of the handle arms 44 or 46 is slidingly movable with respect to the other handle arm 44 or 46 for moving the clamp 28 to the opened or closed position.

Changes may be made in the construction or the operation of the various components, elements and assemblies of the hand instruments described herein and changes may be made to the steps or the sequence of steps of the methods described herein without departing from the spirit and scope of the invention as defined in the following claims.

What is claimed is:

1. An orthodontic's hand instrument for installing a lingual bar on the lingual side of a patient's lower teeth comprising:
 a handle having a first end and a second end, the handle comprising:
  a first handle arm having a first end and a second end; and
  a second handle arm having a first end and a second end, a first portion of the first handle arm near the first end of the first handle arm being connected to a first portion of the second handle arm near the first end of the second handle arm, the first and the second handle arms each having a second portion extending from the first portion to the second ends of the first and the second handle arms with the second portion of the first and the second handle arms extending angularly away from each other and being spaced a distance apart, the first handle arm being springly movable away from the second handle arm and the first handle arm being compressible toward the second handle arm; and
 a clamp connected to the second end of the handle, the clamp having a first clamp portion extending a distance downwardly from the handle terminating with a lower end and having a second clamp portion connected to the lower end of the first clamp portion and extending a distance at an angle from the first clamp portion in a direction generally toward the first end of the handle terminating with a clamp end of the clamp, the handle being manipulatable by the dentist to move the clamp to an opened position whereby the clamp end is insertable over a portion of the lingual bar, and the handle being manipulatable by the dentist for moving the clamp to a closed position whereby the clamp end is clampingly closed over a portion of the lingual bar for clampingly holding the lingual bar, the clamp with the lingual bar held by the clamp being movable into the patient's mouth and lowerable to position the lingual bar near the lingual side of the patient's lower teeth for connecting the lingual bar to the lingual side of the patient's lower teeth.

2. The orthodontic's hand instrument of claim 1 wherein the handle and the clamp are sized for insertion into the patient's mouth.

3. The orthodontic's hand instrument of claim 1 wherein the clamp is defined further as being moved to the closed position when the first and the second handle arms are compressingly moved away from each other and the clamp being moved to the opened position when the first and the second hand arms are compressingly moved away from each other.

4. The orthodontic hand instrument of claim 1 wherein the clamp is defined further as being movable to the opened position when the first and the second handle arms are springly moved away from each other and being movable to the opened position when the first and the second handle arms are compressingly moved toward each other.

5. The orthodontic's hand instrument of claim 1 wherein the clamp is defined further to comprise:
 a first clamp arm having a first end and a second end, the first end of the first clamp arm being connected to the second end of the first handle arm and the first clamp arm extending a distance from the first handle arm;
 a second clamp arm having a first end and a second end, the first end of the second clamp arm being connected to the second end of the second handle arm and the second clamp arm extending a distance from the second handle arm;

a third clamp arm having a first end and a second end, the first end of the third clamp arm being connected to the second end of the first clamp arm and the third clamp arm extending a distance from the first clamp arm in a direction generally toward the first end of the handle; and a fourth clamp arm having a first end and a second end, the first end of the fourth clamp arm being connected to the second clamp arm and the fourth clamp arm extending a distance from the second clamp arm in a direction generally toward the first end of the handle, the second ends of the third and the fourth arms forming the clamp end of the clamp.

6. The orthodontic's hand instrument of claim 5 wherein the first clamp arm extends at an angle about perpendicularly to the first handle arm, and wherein the second clamp arm extends a distance about perpendicularly from the second handle arm, and wherein the third clamp arm extends a distance about perpendicularly from the first clamp arm, and wherein the fourth clamp arm extends about perpendicularly from the second clamp arm.

7. The orthodontic's hand instrument of claim 1 wherein the clamp is defined further to comprise:

a first clamp arm having a first end and a second end, the first end of the first clamp arm being connected to the second end of the first handle arm and the first clamp arm extending a distance from the first handle arm;

a second clamp arm having a first end and a second end, the first end of the second clamp arm being connected to the second end of the second handle arm and the second clamp arm extending a distance from the second handle arm;

a third clamp arm having a first end and a second end, the first end of the third clamp arm being connected to the second end of the first clamp arm and the third clamp arm extending a distance from the first clamp arm in a direction generally toward the first end of the handle;

a fourth clamp arm having a first end and a second end, the first end of the fourth clamp arm being connected to the second clamp arm and the fourth clamp arm extending a distance from the second clamp arm in a direction generally toward the first end of the handle, the second ends of the third and the fourth arms forming the clamp end of the clamp; and wherein the fourth clamp arm extends a distance from the second clamp arm and crosses the third clamp arm whereby a portion of the fourth clamp arm near the second end of the fourth clamp arm is disposed below a portion of the third clamp arm near the second end of the third clamp arm.

8. The orthodontic's hand instrument of claim 7 wherein the first and the second handle arms are defined further as being movable in a direction generally toward each other for moving the third and the fourth clamp arms generally toward each other to the closed position of the clamp, and wherein the first and the second handle arms are defined further as being springingly movable in directions generally away from each other for moving the third and the fourth clamp arms in directions generally away from each other to position the clamp in the opened position.

9. An orthodontic's hand instrument comprising:

a lingual bar;

a handle having a first end and a second end, the handle comprising:

a first handle arm having a first end and a second end; and a second handle arm having a first end and a second end, a first portion of the first handle arm near the first end of the first handle arm being connected to a first portion of the second handle arm near the first end of the second handle arm, the first and the second handle arms each having a second portion extending from the first portion to the second ends of the first and the second handle arms with the second portion of the first and the second handle arms extending angularly away from each other and being spaced a distance apart, the first handle arm being springly movable away from the second handle arm and the first handle arm being compressible toward the second handle arm;

a clamp connected to the second end of the handle, the clamp having a first clamp portion extending a distance downwardly from the handle terminating with a lower end and having a second clamp portion connected to the lower end of the first clamp portion and extending a distance at an angle from the first clamp portion in a direction generally toward the first end of the handle terminating with a clamp end of the clamp, the handle being manipulatable by the dentist to move the clamp to an opened position whereby the clamp end is insertable over a portion of the lingual bar, and the handle being manipulatable by the dentist for moving the clamp to a closed position whereby the clamp end is clampingly closed over a portion of the lingual bar for clampingly holding the lingual bar, the clamp with the lingual bar held by the clamp being movable into the patient's mouth and lowerable to position the lingual bar near the lingual side of the patient's lower teeth for connecting the lingual bar to the lingual side of the patient's lower teeth.

10. The orthodontic's hand instrument of claim 9 wherein the handle and the clamp are sized for insertion into the patient's mouth.

11. The orthodontic's hand instrument of claim 9 wherein the clamp is defined further as being moved to the closed position when the first and the second handle arms are compressingly moved away from each other and the clamp being moved to the opened position when the first and the second hand arms are compressingly moved away from each other.

12. The orthodontic hand instrument of claim 9 wherein the clamp is defined further as being movable to the opened position when the first and the second handle arms are springly moved away from each other and being movable to the opened position when the first and the second handle arms are compressingly moved toward each other.

13. The orthodontic's hand instrument of claim 9 wherein the clamp is defined further to comprise:

a first clamp arm having a first end and a second end, the first end of the first clamp arm being connected to the second end of the first handle arm and the first clamp arm extending a distance from the first handle arm;

a second clamp arm having a first end and a second end, the first end of the second clamp arm being connected to the second end of the second handle arm and the second clamp arm extending a distance from the second handle arm;

a third clamp arm having a first end and a second end, the first end of the third clamp arm being connected to the second end of the first clamp arm and the third clamp arm extending a distance from the first clamp arm in a direction generally toward the first end of the handle; and a fourth clamp arm having a first end and a second end, the first end of the fourth clamp arm being connected to the second clamp arm and the fourth clamp arm extending a distance from the second clamp arm in a direction generally toward the first end of the handle, the second ends of the third and the fourth arms forming the clamp end of the clamp.

14. The orthodontic's hand instrument of claim 13 wherein the first clamp arm extends at an angle about perpendicularly to the first handle arm, and wherein the second clamp arm extends a distance about perpendicularly from the second handle arm, and wherein the third clamp arm extends a distance about perpendicularly from the first clamp arm, and wherein the fourth clamp arm extends about perpendicularly from the second clamp arm.

15. The orthodontic's hand instrument of claim 9 a first clamp arm having a first end and a second end, the first end of the first clamp arm being connected to the second end of the first handle arm and the first clamp arm extending a distance from the first handle arm;

a second clamp arm having a first end and a second end, the first end of the second clamp arm being connected to the second end of the second handle arm and the second clamp arm extending a distance from the second handle arm;

a third clamp arm having a first end and a second end, the first end of the third clamp arm being connected to the second end of the first clamp arm and the third clamp arm extending a distance from the first clamp arm in a direction generally toward the first end of the handle;

a fourth clamp arm having a first end and a second end, the first end of the fourth clamp arm being connected to the second clamp arm and the fourth clamp arm extending a distance from the second clamp arm in a direction generally toward the first end of the handle, the second ends of the third and the fourth arms forming the clamp end of the clamp; and wherein the fourth clamp arm extends a distance from the second clamp arm and crosses the third clamp arm whereby a portion of the fourth clamp arm near the second end of the fourth clamp arm is disposed below a portion of the third clamp arm near the second end of the third clamp arm.

16. The orthodontic's hand instrument of claim 15 wherein the first and the second handle arms are defined further as being movable in a direction generally toward each other for moving the third and the fourth clamp arms generally toward each other to the closed position of the clamp, and wherein the first and the second handle arms are defined further as being springingly movable in directions generally away from each other for moving the third and the fourth clamp arms in directions generally away from each other to position the clamp in the opened position.

17. A method for installing a lingual bar on the lingual side of a patient's lower teeth comprising:
providing the lingual bar;
providing a hand instrument comprising a handle having a first end and a second end, and a clamp connected to the second end of the handle, the clamp having a first clamp portion extending a distance downwardly from the handle terminating with a lower end and a second clamp portion connected to the lower end of the first clamp portion and extending a distance at an angle from the first clamp portion in a direction generally toward the first end of the handle terminating with a clamp end, the clamp being movable to an opened position and to a closed position by the dentist manipulating the handle; and
manipulating the handle to move the clamp to the opened position;
positioning the clamp end over a portion of the lingual bar;
manipulating the handle to move the clamp to the closed position for clampingly engaging and clampingly holding the lingual bar in the clamp;
moving the clamp into the patient's mouth and downwardly to positioning the lingual bar adjacent the lingual side of the patient's lower teeth;
connecting the lingual bar to the lingual side of the patient's lower teeth;
manipulating the handle to move the clamp to the opened position thereby releasing the clamping engagement with the lingual bar; and
removing the clamp of the handle instrument from the lingual bar and removing the clamp from the patient's mouth thereby leaving the lingual bar positioned adjacent the lingual side of the patient's lower teeth.

18. The method of claim 17 wherein the step of moving the clamp into the patient's mouth is defined further as moving the clamp into the patient's mouth beyond the patient's lower teeth and then moving the clamp downwardly and back in a direction out of the patient's mouth and positioning the lingual bar adjacent the lingual side of the patient's lower teeth.

19. The method of claim 17 wherein the step of providing the hand instrument is further defined as providing the had instrument with the handle further comprising: a first handle arm having a first end and a second end; and a second handle arm having a first end and a second end, a first portion of the first handle arm near the first end of the first handle arm being connected to a first portion of the second handle arm near the first end of the second handle arm, the first and the second handle arms each having a second portion extending from the first portion to the second ends of the first and the second handle arms with the second portion of the first and the second handle arms extending angularly away from each other and being spaced a distance apart, the first handle arm being springly movable away from the second handle arm and the first handle arm being compressible toward the second handle arm.

20. The method of claim 19 wherein the step of providing the hand instrument is defined further as providing the hand instrument with the clamp being moved to the closed position when the first and the second handle arms are compressingly moved away from each other and the clamp being moved to the opened position when the first and the second hand arms are compressingly moved away from each other.

21. The method of claim 19 wherein the step of providing the hand instrument is defined further as providing the had instrument with the clamp being movable to the opened position when the first and the second handle arms are springly moved away from each other and being movable to the opened position when the first and the second handle arms are compressingly moved toward each other.

22. The method of claim 19 wherein the step of providing the hand instrument is defined further as providing the had instrument with the clamp having a first clamp arm having a first end and a second end, the first end of the first clamp arm being connected to the second end of the first handle arm and the first clamp arm extending a distance from the first handle arm; a second clamp arm having a first end and a second end, the first end of the second clamp arm being connected to the second end of the second handle arm and the second clamp arm extending a distance from the second handle arm; a third clamp arm having a first end and a second end, the first end of the third clamp arm being connected to the second end of the first clamp arm and the third clamp arm extending a distance from the first clamp arm in a direction generally toward the first end of the handle; and a fourth clamp arm having a first end and a second end, the first end of the fourth clamp arm being connected to the second clamp arm and the fourth clamp arm extending a distance from the second clamp arm in a direction generally toward the first end of the handle, the second ends of the third and the fourth arms forming the clamp end of the clamp.

23. The method of claim 22 wherein the step of providing the hand instrument is defined further as providing the hand instrument with the first clamp arm extending at an angle about perpendicularly to the first handle arm, and the second clamp arm extending a distance about perpendicularly from the second handle arm, the third clamp arm extending a distance about perpendicularly from the first clamp arm, and the fourth clamp arm extending about perpendicularly from the second clamp arm.

24. The method of claim 19 wherein the step of providing the hand instrument is defined further as providing the hand instrument with the clamp having a first clamp arm having a first end and a second end, the first end of the first clamp arm being connected to the second end of the first handle arm and the first clamp arm extending a distance from the first handle arm; a second clamp arm having a first end and a second end, the first end of the second clamp arm being connected to the second end of the second handle arm and the second clamp arm extending a distance from the second handle arm; a third clamp arm having a first end and a second end, the first end of the third clamp arm being connected to the second end of the first clamp arm and the third clamp arm extending a distance from the first clamp arm in a direction generally toward the first end of the handle; a fourth clamp arm having a first end and a second end, the first end of the fourth clamp arm being connected to the second clamp arm and the fourth clamp arm extending a distance from the second clamp arm in a direction generally toward the first end of the handle, the second ends of the third and the fourth arms forming the clamp end of the clamp; and wherein the fourth clamp arm extends a distance from the second clamp arm and crosses the third clamp arm whereby a portion of the fourth clamp arm near the second end of the fourth clamp arm is disposed below a portion of the third clamp arm near the second end of the third clamp arm.

25. The method of claim 24 wherein the step of providing the hand instrument is defined further as providing the hand instrument with the first and the second handle arms being movable in a direction generally toward each other for moving the third and the fourth clamp arms generally toward each other to the closed position of the clamp, and wherein the first and the second handle arms are defined further as being springingly movable in directions generally away from each other for moving the third and the fourth clamp arms in directions generally away from each other to position the clamp in the opened position.

* * * * *

UNITED STATES PATENT AND TRADEMARK OFFICE
CERTIFICATE OF CORRECTION

PATENT NO. : 5,261,813

DATED : November 16, 1993

INVENTOR(S) : Melvin B. Baker

It is certified that error appears in the above-identified patent and that said Letters Patent is hereby corrected as shown below:

Column 6, Line 1; before handle, please insert --a--.

Column 10, Line 50; after the, please delete "had" and substitute therefore --hand--.

Column 11, Line 7; after the, please delete "had" and substitute therefore --hand--.

Column 11, Line 16; after the, please delete "had" and substitute therefore --hand--

Signed and Sealed this

Fourteenth Day of June, 1994

Attest:

BRUCE LEHMAN

Attesting Officer

Commissioner of Patents and Trademarks